(12) United States Patent
Piccolo et al.

(10) Patent No.: US 6,548,693 B2
(45) Date of Patent: Apr. 15, 2003

(54) NITRILOXY DERIVATIVES OF (R) AND (S)-CARNITINE

(75) Inventors: Oreste Piccolo, Sirtori (IT); Roberto Castagnani, Recanati (IT); Paolo De Witt, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/119,954

(22) Filed: Apr. 11, 2002

(65) Prior Publication Data

US 2002/0119965 A1 Aug. 29, 2002

Related U.S. Application Data

(62) Division of application No. 09/804,270, filed on Mar. 13, 2001, now Pat. No. 6,395,923, which is a continuation of application No. PCT/IT00/00325, filed on Jul. 31, 2000.

(30) Foreign Application Priority Data

Aug. 5, 1999 (IT) .......................... RM99A0508

(51) Int. Cl.⁷ .................. C07C 203/00; C07C 229/00; C07C 69/66
(52) U.S. Cl. ................. 558/483; 562/567; 560/176
(58) Field of Search .................. 562/567, 176; 558/483

(56) References Cited

U.S. PATENT DOCUMENTS 3,830,931 A  8/1974 De Felice
5,214,166 A * 5/1993 Manser et al.
5,227,513 A  7/1993 Meul
5,532,410 A * 7/1996 Giannessi et al.
6,365,611 B1 * 4/2002 Konig et al.

FOREIGN PATENT DOCUMENTS

| DE | 98/56759 | * | 6/1998 |
|---|---|---|---|
| DE | WO98/56759 | | 12/1998 |
| EP | 0 609 643 | | 8/1994 |
| EP | 0 624 568 | | 11/1994 |
| EP | 0 636 603 | | 2/1995 |

* cited by examiner

Primary Examiner—Johann Richter
Assistant Examiner—Paul A. Zucker
(74) Attorney, Agent, or Firm—Nixon & Vanderhye P.C.

(57) ABSTRACT

Carnitine derivatives of formula (I) are described in racemic and/or optically active form, as well as the process for their preparation and their use as pharmaceutical anti-angina active ingredients for the treatment of ischaemic heart disease.

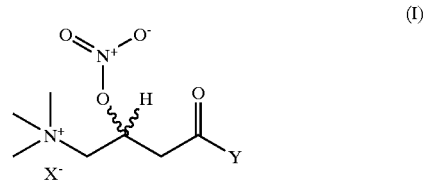

Also described is a process for producing the (R)-carnitine enantiomer from (S)-carnitine (or vice versa), using the derivatives of formula (I).

13 Claims, No Drawings

NITRILOXY DERIVATIVES OF (R) AND (S)-CARNITINE

This application is a divisional of Ser. No. 09/804,270 filed Mar. 13, 2001, now U.S. Pat. No. 6,395,923, which is a continuation of PCT/IT00/00325 filed Jul. 31, 2000.

FIELD OF THE INVENTION

The invention described herein relates to derivatives of (R) and (S)-carnitine, and particularly nitriloxy derivatives which are useful as intermediate synthesis products and as therapeutic agents.

BACKGROUND OF THE INVENTION

Organ ischaemia is caused by an imbalance between the oxygen requirements of the tissue and oxygen availability from the bloodstream. In the particular case of cardiac ischaemia, this manifests with typical symptoms, known as *angina pectoris*. The causes are multiple and, among them, we should mention the reduced ability of the coronary circulation to supply oxygen, owing, for example, to the presence of atheromatous plaques. One possible consequence of the ischaemia is myocardial infarction.

Myocardial ischaemia may also be asymptomatic and detectable only by means of clinical and instrumental examinations.

The therapy currently available is based mainly on the administration of coronary dilating drugs, which, on account of the specific needs of symptomatological treatment, have to have as rapid an action as possible. Calcium antagonists, β-adrenergic antagonists and antiaggregant agents should also be mentioned.

Among the drugs still most commonly used today, we should mention the organic nitrates, which by releasing NO at the action site exert a local vasodilatory action.

Amyl nitrite is used by inhalation in cases of angina attack. Nitroglycerine and organic nitrates of higher molecular weight are also used for the prevention of such attacks. Nitroderivatives are associated with a series of important side effects. The most common of these is headache, which may even be very severe. More serious is the fact that these drugs give rise to tolerance and their withdrawal causes a rebound effect. Nitroglycerine is also administered using transdermal release systems, which, however well designed they may be, present problems in their own right, such as those relating to permanence at the application site, controlled delivery of the drug and patient compliance.

Calcium antagonists present the problem of excessive vasodilatation, with consequent dizziness, hypotension, headache, and nausea, and it is by no means easy to establish the appropriate therapeutic regimen.

β-antagonists have effects on cardiac haemodynamics.

For a more detailed discussion of these aspects, the reader is referred to Goodman & Gilman's The Pharmacological Basis of Therapeutics-9th edition, chapter 32.

To date, no single drug therapy is available for the treatment of ischaemic states, particularly *angina pectoris*, which possesses the desired characteristics in terms of patient compliance, safety of use, lack of side effects and immediacy of action. In particular, no ester of nitric acid is as yet available which combines the characteristics of immediacy of action and a lack of the side effects typical of this class of drugs.

Patent application WO98/56759 describes pentaerythrite derivatives of general formula $(O_2NOCH_2)_m C(CH_2OH)_n (CH_2COR^1)_o (COR^1)_p$. The multiple meanings of $R^1$ include nitriloxy derivatives of carnitine, in particular nitriloxy-carnitine chloride, its inner salt and ester with (1-alkoxy-carbonylmethyl-2-trialkylammonium)ethanol. An ester of racemic nitriloxy-carnitine with (1-alkoxycarbonylmethyl-2-trialkyl-ammonium) ethyl alcohol is also envisaged, provided on mixtures containing equimolar amounts of (R) and (S) isomers. The anti-angina activity of these compounds is mentioned in the description. Nitriloxy-carnitine is also prepared as an intermediate. The examples of the compounds are provided on the racemic mixtures. The only example of a preparation, example 17, which uses L-carnitine, envisages reaction with the chloride of 3-nitriloxy-2,2-bis(nitriloxymethyl)propionic acid. The resulting compound (not identified either in physico-chemical or in structural terms) is not included in the claims and is not mentioned in relation to its presumed pharmacological activity. The patent application cited does not provide a general scheme for preparation of the compounds, and thus the compounds effectively described are to be found in the preparation examples. No pharmacological activity data are provided.

The action of L-carnitine in the treatment of heart failure is known (U.S. Pat. No. 3,830,931).

Also known is the fact that acetyl L-carnitine enhances the oxidation of glucose and prevents the accumulation of lactate in the concomitant acidosis (Lopaschuk, G. in *Carnitine Today*—C. De Simone and G. Famularo ed.) Lands Bioscience 1997).

Alkanoyl derivatives of L-carnitine are known for different uses in human or animal therapy.

It has now surprisingly been found that enantiomerically enriched nitriloxy derivatives of (R) or (S)-carnitine are endowed with favourable and advantageous pharmacological activities, particularly as therapeutic agents for organ ischaemias, and even more particularly for the treatment of *angina pectoris*.

Nitriloxy derivatives of (R) and (S)-carnitine are also useful intermediates for synthesis for the production of chiral 3–4 carbon atom synthons having the (R) or (S) configuration, such as for example 3-hydroxy-γ-butyrolactone, 1,2,4-butantriole, 3-hydroxytetrahydrofurane, 3-hydroxypyrrolidine, 2,3-dihydroxypropylamine, to be used in the industrial synthesis of enantiomerically pure drugs. However, (R) and (S)-carnitine are not actually available at low cost, therefore a process convenient and applicable on a large scale, allowing the stereospecific conversion of (S)-carnitine into (R)-carnitine or vice-versa will be economically advantageous and useful.

It has now surprisingly been found that enantiomerically enriched nitriloxy derivatives of (S)-carnitine, according to the present invention, are suitable intermediates for the production of (R)-carnitine its derivatives, and vice-versa.

ABSTRACT OF THE INVENTION

The subject of the invention described herein are carnitine derivatives of general formula (I) in optically active form of absolute configuration (R) or (S)

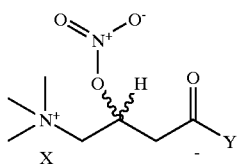

(I)

where

Y is an OR or NR¹R2 group with

R equal to hydrogen, $C_1$–$C_{10}$ alkyl or alkyl substituted with $C_6$–$C_{10}$ (aryl, said aryl optionally carrying one or more $C_1$–$C_4$ alkyls;

$R^1$ and $R^2$, which may be the same or different, are hydrogen, $C_1$–$C_{10}$ alkyl or alkyl substituted with $C_6$–$C_{10}$ aryl, said aryl optionally carrying one or more $C_1$–$C_4$ alkyls; or, taken together, form a 5–7 atom heterocyclic ring with the nitrogen atom;

or Y is the residue of an esterified polyalcohol with at least one nitric acid equivalent;

X- is the anion of a pharmaceutically acceptable organic or inorganic acid, or, if Y is an OH group, the formula (I) product may exist in the form of an inner salt, i.e. with structure (II)

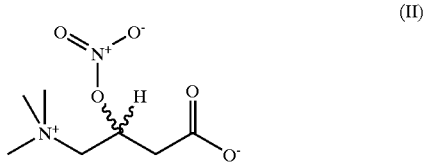

(II)

and their enantiomerically enriched mixtures.

Examples of $C_1$–$C_{10}$ alkyls are methyl, ethyl propyl, butyl, pentyl, hexyl, octyl, nonyl, decyl and all their possible isomers.

Examples of substituted alkyls are benzyl and phenylethyl.

Examples of substituted aryls are tolyl, xylyl and its isomers.

Examples of polyalcohols are glyceryl mono- or dinitrate, isosorbide mononitrate, erythrityl di- o trinitrate, pentaerythrityl mono-, di- or trinitrate.

Examples of anions of organic or inorganic acids are $NO_3^-$, $Cl^-$, $Br^-$, $I^-$, $HSO_4^-$, $(SO_4^{2-})_{0.5}$, $H_2PO_4^-$, $(HPO_4^{2-})_{0.5}$, $(PO_4^{3-})_{0.33}$, a residue of a hydroxy acid, a residue of a bicarboxylic acid, $OSO_2Z^-$, $OCOZ^-$ or $OCOH^-$ with Z equal to $C_1$–$C_{10}$ alkyl, substituted alkyl, such as, for example, trihalomethyl or benzyl, aryl, such as, for example, phenyl, tolyl, halophenyl or alkoxyphenyl. What is meant by halogen is fluorine, chlorine, bromine and iodine. Preferred examples of anions of organic and inorganic acids are those derived from pharmaceutically acceptable acids, among which, in addition to those exemplified above, we would mention particularly mandelate, orotate, acid aspartate, acid citrate, fumarate and acid fumarate, maleate and acid maleate, mucate, malate and acid malate, glucose phosphate, tartrate and acid tartrate, succinate, acid succinate, oxalate.

Examples of a heterocyclic ring with 5–7 nitrogen atoms are tetrahydropyrrhol, piperidine, piperazine, morpholine, alkyl-morpholine and azepine.

Compounds whose absolute configuration is (R) are preferred.

Additionally preferred are compounds whose absolute configuration is (R) and in which $X^-$ is an anion of a pharmaceutically acceptable acid, namely the compound of formula (I) in the form enantiomerically enriched of absolute configuration (R).

A further subject of the invention described herein is the process for the preparation of formula (I) or (II) compounds, using procedures which are in themselves known, starting from formula (III) compounds with known nitrating agents, such as, for example, concentrated nitric acid, a nitric acid/sulphuric acid mixture, a nitric acid/acetic anhydride mixture, etc., when T is a hydroxy group or when T is a good leaving group; or by means of treatment with alkaline nitrates, earth-alkaline nitrates, silver nitrate, ammonium nitrate or tetra-alkylammonium nitrate, when T is a good leaving group, such as, for example, an $OSO_2Z$ group, where Z is as defined above.

DETAILED DESCRIPTION OF THE INVENTION

The process is illustrated in the following scheme:

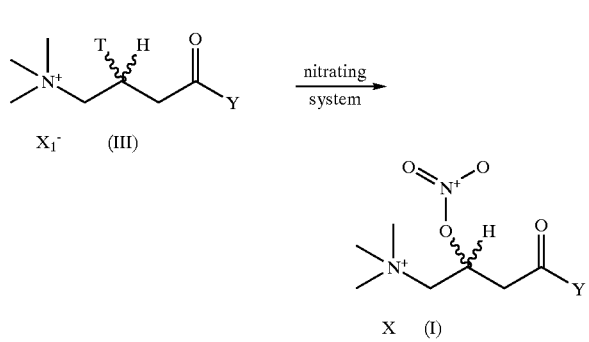

where T is a hydroxy group or T is a leaving group, $X_1^-$, equal to or different from $X^-$, being included in the meanings illustrated above.

The $X^-$ group, as required and using techniques in themselves known, such as the use of ion-exchange resins or by means of electrodialysis, can be varied in the context of the possibilities listed above, subsequent to treatment with the nitrating system.

Formula (III) products are optically active and, according to the nitrating system used, formula (I) products can be obtained, with the same absolute configuration as the formula (III) products or with the opposite absolute configuration, and, to be precise, retention of absolute configuration occurs when the nitrating agent used in the course of the reaction does not involve the formation of a bond with the asymmetric carbon atom, while inversion of configuration is observed when using nitrating agents whose mechanism of action involves an $S_N2$ nucleophilic substitution reaction with substitution of the T group.

A further subject of the invention described herein is the use of formula (I) compounds, and particularly of derivatives with Y equal to an OH group and $X^-$ equal to $NO_3^-$, $Cl^-$, $OSO_2Z^-$ or $OCOZ^-$ with Z equal to $C_1$–$C_{10}$ alkyl, or of the formula (II) compound, preferably in the optically active form of absolute configuration (R) and in the case of enantiomerically enriched mixtures, said mixtures preferably comprising an amount of the enantiomer (R) higher than 95%, as pharmaceutically active anti-angina ingredients in solid and liquid pharmaceutical compositions for oral administration, parenteral administration, transdermal use or sublingual use in the treatment of ischaemic heart disease.

Said compositions include a pharmaceutically effective dose of the active ingredient, optionally in mixtures with pharmaceutically acceptable vehicles or excipients. The invention described herein also relates to a therapeutic method for the treatment of *angina pectoris* and of various ischaemic forms, comprising the administration of said compositions in amounts corresponding to 1–200 mg of active ingredient per day orally, of 0.1–100 mg of active ingredient per day parenterally, or of equivalent effective daily doses of active ingredient sublingually or transdermally, preferably 0.1–200 mg of active ingredient per day sublingually, and 0.1–100 mg of active ingredient per day transdermally.

A further aspect of the invention described herein is a process for producing (R)-carnitine on an industrial scale starting from the corresponding (S) enantiomorph, which is a raw material available in large amounts and at low cost, in that it is easily obtainable as a by-product of industrial processes of resolution of the racemic mixture of (R,S)-carnitine or (R,S)-carnitinamide with optically active acids such as tartaric acid, tartaric dibenzoyl acid, camphoric acid or camphorsulphonic acid, by means of the formation of derivatives of general formula (I) or (II).

A number of processes have recently been described for the production of (R)-carnitine starting from the corresponding (S) enantiomer; in particular, in U.S. Pat. Nos. 5,412,113 and 5,599,978 (S) carnitine is esterified to protect the carboxylic group; the ester thus obtained is then converted to the corresponding mesylate and subsequently subjected to hydrolysis to restore the carboxylic group; at a suitable pH value, a chiral lactone is formed which presents the desired (R) configuration which then yields (R)-carnitine by basic hydrolysis. This process, however, is not free of drawbacks, owing both to the fact that one has to protect and then deprotect the carboxylic function and because for formation of the mesylate to take place with good yields an excess of methane sulphonic anhydride has to be used with consequent formation of large amounts of methane sulphonic acid as a by-product, as well as because the formation of fairly large amounts of crotonoylbetaine as a by-product is possible.

In contrast, the process according to the present invention, which uses formula (I) derivatives, and preferably the one with Y=OH and $X^-=NO_3^-$, of absolute configuration (S), or the formula (II) compound of absolute configuration (S), easily obtainable starting from (S)-carnitine by treatment with acid nitrating mixtures, makes it possible to obtain (R)-carnitine, in a very simple manner, with a lower number of steps, a high yield and high stereospecificity, by treatment with inorganic and organic bases of the aforementioned formula (I) or (II) products in water or in mixtures of water and organic solvent mixable in water, operating at a pH value ranging from 7 to 10, and preferably at a pH value ranging from 7.5 to 9.5 and even more preferably from 8 to 9 and at a temperature of 50–100° C. and preferably at a temperature of 60–80° C. This process may occur even without isolation of the (I) or (II) derivatives and thus allow "one pot" transformation of (S)-carnitine to (R)-carnitine. The preferred bases are bicarbonates of alkaline or alkaline-earth metals and potassium phthalimide.

Though of less industrial interest at this time, the inverse process for transforming (R)-carnitine into (S)-carnitine is obviously feasible with the same process.

A further aspect of the invention described herein is the process for preparing (R)-carnitine from (S)-carnitine or vice versa through the use of the formula (IV) intermediate enantiomerically enriched of absolute configuration (R) and (S), respectively, prepared in any way and preferably starting from a formula (I) derivative with Y=OR or $NR^1R^2$ with R=H, $C_1$–$C_{10}$ alkyl, or substituted alkyl and where $R^1R^2$, equal or different from one another, are alkyl, hydrogen $R^1R^2$ and $X^-=NO_3^-$ by treatment with organic or inorganic bases in water or in mixtures of water and organic solvent mixable with water.

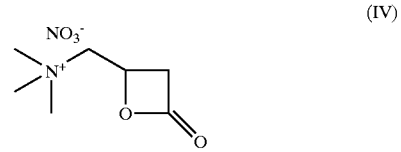

(IV)

The following examples further illustrate the invention.

EXAMPLE 1

Preparation of (R)-3-Nitriloxy-Carnitine Nitrate

A solution of (R)-carnitine (20 g; e.e. >99%),) in 65% nitric acid (178 g), cooled to 0–5° C., is slowly added to 98% acetic anhydride (652.2 g) in the space of 12 h. On completing the addition, the mixture is brought back up to room temperature and maintained under stirring for a further 6 h and then diluted with isopropyl ether (0.6 l), with the formation, in the space of 1–2 h, of a white solid which is filtered, washed with isopropyl ether and dried to yield (R)-3-nitriloxy-carnitine nitrate (27.8 g; yield 83%), with a melting point of 125.5–127° C. and rotatory power $[\alpha]_D^{25}=-34.66$, $[\alpha]_D^{20}=-36.7$ (c=10%, $H_2O$). $^1$H-NMR spectrum ($D_2O$): δ5.85–6.00 [m,1H,—$C\underline{H}(ONO_2)^-$]; 3.75–4.05 [m,2H,—$C\underline{H}_2$—$N^+(CH_3)_3$)]; 3.25 [s,9H,$N^+(C\underline{H}_3)_3$)]; 2.85–3.20 [m, 2H,—$C\underline{H}_2$—COOH] in ppm.

Elemental analysis: C 30.98; H 5.41; N 15.38.

EXAMPLE 2

Preparation of (R)-3-Nitriloxy-Carnitine Nitrate

A solution of (R)-carnitine (20 g; e.e. >99%) in 65% nitric acid (88 g), cooled to 5° C., is slowly added to 98% acetic anhydride (200 g) in the space of 2 h. On completing the addition, the mixture is maintained at 5–10° C. for 3.5 h. After a work-up similar to that in the previous example, (R)-3-nitriloxy-carnitine nitrate was obtained (26.8 g; yield 80%).

EXAMPLE 3

Preparation of (R)-3-Nitriloxy-Carnitine Nitrate

The preparation is done as in example 1, but, at the end of the reaction, most of the excess $HNO_3$ and acetic acid is distilled off at reduced pressure (10 mm Hg).

The residue is then precipitated by addition of ethyl acetate (0.4 l) to obtain (R)-3-nitriloxy-carnitine nitrate with comparable characteristics.

EXAMPLE 4

Preparation of (S)-3-Nitriloxy-Carnitine Nitrate

A solution of (S)-carnitine (1 g; e.e. >99%) in 65% nitric acid (8.9 g), cooled to 0–50° C., is slowly added to 98% acetic anhydride (27.3 g) in the space of 1 h. On completing the addition, the mixture is brought back up to room temperature and maintained under stirring for a further 6 h and then diluted with ethyl ether (75 ml), with the formation, in the space of 2 h, of a white solid that is filtered, washed with ether and dried to yield (S)-3-nitriloxy-carnitine nitrate (1.33 g; yield 80%), with a melting point of 125.5–127° C. and rotatory power $[\alpha]_D^{25}=+34.97$ (c=10% $H_2O$).

EXAMPLE 5
Preparation of (R)-Carnitine

A solution of (S)-3-nitriloxy-carnitine nitrate (1 g), obtained according to the process in example 4, in water (20 ml) is added to NaHCO$_3$ (0.62 g) and heated to 60° C. for 66 h. The complete quantitative conversion of the starting product to (R)-carnitine nitrate is obtained, with e.e. >99%. The product thus obtained in aqueous solution was converted to the inner salt by treatment with ion-exchange resins; by subsequent concentration of the aqueous solution and crystallization, 0.8 g of (R)-carnitine was obtained with rotatory power $[\alpha]_D^{25}=-30.5$ (c=10% H$_2$O).

EXAMPLE 6
Preparation of (R)-Carnitine

Operating as in example 5, but working at 80° C., the reaction is complete after 8 h.

EXAMPLE 7
Preparation of (R)-Carnitine

A solution of (S)-3-nitriloxy-carnitine nitrate (1 g), obtained according to the process in example 4, in water (20 ml) is added to NaHCO$_3$ (0.62 g) and heated to 60° C. for 66 h. The complete quantitative conversion of the starting product to (R)-carnitine nitrate is obtained, with e.e. >99%. The product thus obtained in aqueous solution was converted to the inner salt by electrodialysis; by subsequent concentration of the aqueous solution and crystallization, 0.7 g of (R)-carnitine were obtained with rotatory power $[\alpha]_D^{25}=-30.1$ (c=10% H$_2$O).

EXAMPLE 8
Preparation of (S)-Nitriloxy-Carnitine Nitrate

65% nitric acid (150 g) is dehydrated by addition of Ac$_2$O at 5° C. (297.7 g). Again at 5° C., (S)-carnitine inner salt (50 g) and more acetic anhydride (31.5 g) are added in sequence. On completing the additions, the reaction is left to proceed at room temperature for 17 h and the excess nitric acid is then distilled at reduced pressure (20 mm Hg). The residue is precipitated by addition of EtOAc (1.2 l) obtaining (S)-3-nitriloxy-carnitine nitrate (66.8 g; yield 80%).

EXAMPLE 9
Preparation of (S)-Nitriloxy-Carnitine Nitrate

65% nitric acid (150 g) is dehydrated by addition of Ac$_2$O at 5° C. (300 g; 3.1 moles). Again at 5° C., (S)-carnitine inner salt (100 g; 0.62 moles) and more acetic anhydride (63 g) are added in sequence. The cooling is then removed and, after 18 h at room temperature, the residue is precipitated with ethyl acetate (2.4 l) to obtain (S)-3-nitriloxy-carnitine nitrate (134 g; yield 80.5%).

EXAMPLE 10
Preparation of (S)-Nitriloxy-Carnitine Nitrate

A solution of (S)-carnitine inner salt (100 g) in 90% HNO$_3$ (215 g) is slowly added to Ac$_2$O (187.5 g), maintaining the temperature between 5 and 10° C.

On completing the addition, the reaction is left to proceed at 5–10° C.

After 2 h the excess nitric acid is evaporated as in example 8 and the residue precipitated with ethyl acetate (2.4 l) to obtain (S)-3-nitriloxy-carnitine nitrate (136 g; yield 81.4%).

EXAMPLE 11
Preparation of (R)-Carnitine Via the β-Lactone Intermediate

A solution of (S)-3-nitriloxy-carnitine nitrate (1 g), obtained according to the process in example 4, in water (20 ml) is added to NaHCO$_3$ (0.31 g) and heated to 45° C.

After 48 h the formation of β-lactone nitrate is noted.
$^1$H-NMR (D$_2$O)=5.25–5.35 (m, 1H), 3.98–3.86 (m, 3H), 3.55–3.45 (dd, 1H), 3.24 (s, 9H).

By treating with an amount of 0.31 g of NaHCO$_3$ and heating to 80° C., (R)-carnitine having an enantiomeric excess higher than 98% is obtained.

EXAMPLE 12
Preparation of (R)-Carnitine Without Isolation of (R)-Nitriloxy-Carnitine Operating as in example 9, but distilling the crude product in the end to remove the nitric acid and most of the acetic acid, instead of precipitating (S)-nitriloxy-carnitine and adding KHCO$_3$ (257 g) directly to the residue suitably diluted with H20 (3.3 l), the complete formation of (R)-carnitine nitrate is obtained by working for 8 h at 80° C.

The product thus obtained in aqueous solution was converted to the inner salt by means of treatment with ion-exchange resins; by subsequent concentration of the aqueous solution and crystallisation, 82 g of (R)-carnitine were obtained with rotatory power $[\alpha]_D^{25}=-28.5$ (c=10% H$_2$O).

EXAMPLE 13
Preparation of (R)-Carnitine Without Isolation of (R)-Nitriloxy-Carnitine To a mixture of (S)-carnitine inner salt (100 g; 0.62 moles) in glacial CH$_3$COOH (100 g) 100% HNO$_3$ is added (117.2 g; 1.86 moles) keeping the temperature at 10° C. and in the space of 1 hour and 5 minutes. Then, the temperature was lowered to 0–5° C. and acetic anhydride was added (76 g; 0.744 moles) in 2 hours and 10 minutes. After keeping the reaction mixture cool (3–5° C.) for further 3 hours from the end of addition, the reaction mass was left at 5° C. overnight. The following morning, temperature was left to rise up to 19° C. and ethyl acetate was added (835 ml) to precipitate nitriloxy-carnitine nitrate. After stirring the suspension for 30', it was filtered washing with ethyl acetate (330 ml). The wet solid on the filter (164,6 g) was dissolved in water (760 ml) and NaHCO$_3$ (94.53 g; 1.125 moles) was added to the solution. Temperature was kept at 80° C. for 9 hours, the solution was diluted with water (760 ml) and passed through IR 120 (H$^+$) (1320 ml) with the purpose to block carnitine. After washing with water, to completely eliminate acidity, elution was made with 1N NH$_3$ and the ammonia solution was concentrated and eliminated with an azeotrope with isobutyl alcohol, giving (R)-carnitine inner salt, having an enantiomeric excess higher than 98% (70.8 g; yield 70.2%).

EXAMPLE 14
Preparation of (R)-Carnitine Via the β-Lactone Intermediate

A solution of (S)-3-nitriloxy-carnitine nitrate (1 g), obtained according to the method of example 4, in N-methylpyrrolidone (20 ml) was added to potassium phthalimide (0.825 g; 0.00446 moles). After 20 h the formation of the β-lactone nitrate was observed.
$^1$H-NMR (D$_2$O)=5.25–5.35 (m, 1H), 3.98–3.86 (m, 3H), 3.55–3.45 (dd, 1H), 3.24 (s, 9H).

What is claimed is:
1. A process for the preparation of a compound of formula (I) in optically active form with absolute configuration (S)

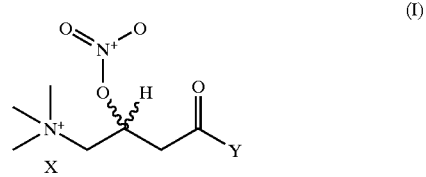

where
Y is OH;
X$^-$ is NO$_3^-$ or a compound of formula (I) in the form of an inner salt of the formula (II)

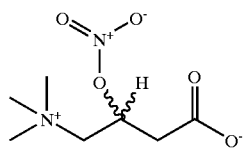
(II)

and their enantiomerically enriched mixtures, comprising treating a formula (III) compound with a nitrating agent not involving the formation of a bond with the asymmetric carbon atom according to the following scheme:

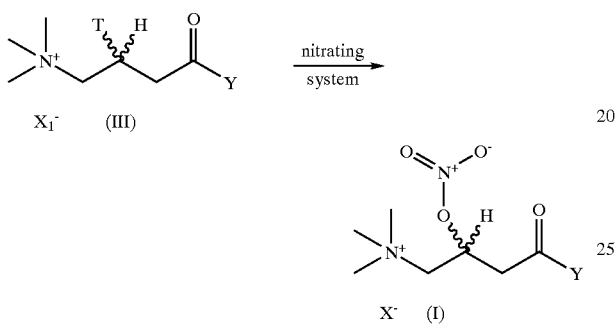

where T is an hydroxy group, $X_1^-$, equal to or different from $X^-$ to yield the formula (I) compound with the same absolute configuration as the formula (III) compound.

2. The process according to claim 1, in which said nitrating agent is a mixture of nitric acid, and acetic anhydride or a mixture of nitric acid, acetic acid and acetic anhydride.

3. The process according to claim 1, in which the $X^-$ group, if required, may be varied subsequent to treatment with the nitrating system.

4. The process according to claim 3, in which the variation of the $X^-$ group is done by ion-exchange resins or electrodialysis.

5. The method according to claim 1, in which an enantiomerically enriched mixture comprises a content of (S) enantiomer higher than 95%.

6. A process for the preparation of (R)-carnitine starting from the corresponding enantiomer (S) of a compound of formula (I) in optically active form with absolute configuration (S)

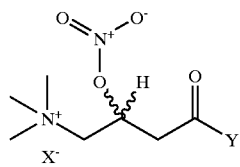
(I)

where
Y is OH;
$X^-$ is $NO_3^-$
or a compound of formula (I) in the form of an inner salt of the formula (II)

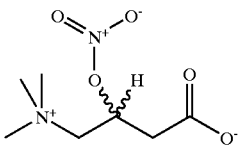
(II)

and their enantiomerically enriched mixtures comprising treating said compound with a diluted base.

7. The process according to claim 6, where said diluted base is sodium bicarbonate.

8. The process according to claim 6, where said base is diluted in water or in mixtures of water and organic solvent mixable with water.

9. The process according to claim 6, where the pH ranges from 7 to 10.

10. The process according to claim 6, where the reaction temperature ranges from 50 to 100° C.

11. A process for the preparation of (R)-carnitine, comprising the following steps:

a) treatment of a formula (III) enantiomer of absolute configuration (S), of claim 1, with a nitrating agent not involving the formation of a bond with the asymmetric carbon atom, to yield the formula (I) compound with the same absolute configuration as the formula (III) compound; and b) treatment of the formula (I) compound with diluted bases.

12. The process according to claim 11, carried out without isolation of the formula (I) compound.

13. A process for the preparation of (R)-carnitine from (S)-carnitine comprising transformation of the formula (I) compound

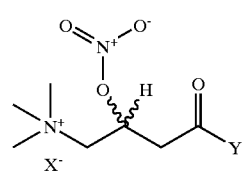
(I)

in which Y=OR or $NR^1R^2$, with R=H, $C_1-C_{10}$ alkyl, or substituted alkyl and where $R^1R^2$, equal or different from one another, are hydrogen, $C_1-C_{10}$ alkyl and $X^-=NO_3^-$, into the formula (IV) compound, enantiomerically enriched of, respectively, absolute configuration (R):

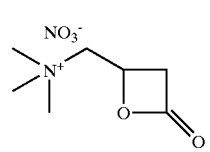
(IV)

with organic or inorganic bases in water or water and organic solvent mixable with water.

* * * * *